United States Patent [19]

Emeury et al.

[11] 4,381,400
[45] Apr. 26, 1983

[54] PROCESS FOR THE SYNTHESIS OF ISOSORBIDE MONONITRATES

[75] Inventors: Jean-Marie Emeury; Eric Wimmer, both of Sorgues, France

[73] Assignee: Societe Nationale Des Poudres et Explosifs, Paris, France

[21] Appl. No.: 349,073

[22] Filed: Feb. 16, 1982

[30] Foreign Application Priority Data

Feb. 27, 1981 [FR] France .................. 81 03906

[51] Int. Cl.$^3$ .......................... C07D 493/04
[52] U.S. Cl. .................................... 549/464
[58] Field of Search ........................ 549/464

[56] References Cited

U.S. PATENT DOCUMENTS 3,886,186 5/1975 Dvonch et al. .................. 549/464

Primary Examiner—Richard Raymond
Attorney, Agent, or Firm—Bucknam and Archer

[57] ABSTRACT

The invention relates to the synthesis of isosorbide mononitrates.

The process according to the invention consists in reacting a hydrazine derivative with isosorbide dinitrate, in a polar solvent medium. The reaction is preferably carried out at the reflux temperature of the solvent medium, with an excess of the hydrazine derivative. A preferred solvent medium is a mixture of tetrahydrofuran and methanol. The process leads to the preferential formation of isosorbitol-2-mononitrate, which is a coronary vasodilator.

12 Claims, No Drawings

PROCESS FOR THE SYNTHESIS OF ISOSORBIDE MONONITRATES

The invention relates to the synthesis of two isosorbide mononitrates and to their separation.

Isosorbitol, or 1,4,3,6-dianhydrosorbitol, is a diol in which the hydroxyl groups are responsible for position isomerism. Thus, there are two isosorbitol mononitrates, generically called MONIS compounds hereafter, depending on whether the nitrated hydroxyl group is the hydroxyl group in the exo-position (MONIS 2) or the one in the endo-position (MONIS 5):

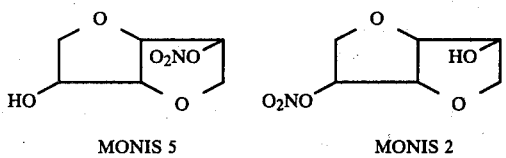

MONIS 5      MONIS 2

The MONIS compounds, and in particular MONIS 2, are known as coronary vasodilators like isosorbitol dinitrate (DINIS) and nitroglycerine. The properties of these compounds as intermediates in the metabolism of DINIS in the blood have been described by R. C. Wendt, J.Pharmacol.exp.Ther. 180, 732–742 (1972), and more recently in La Nouvelle Presse Medicale, Volume 9, pages 2,424 to 2,427 (1980).

Hitherto, as far as is known, there have existed two processes for the synthesis of the MONIS compounds. The earlier process was described by Csizmadia and Hayward in Photochem.Photobiol. 4, 657 (1965), and consists in nitrating isosorbitol directly. This process, which was repeated in U.S. Pat. No. 3,886,186, has serious disadvantages which lie not so much in the difficulty of separating the mixture of isomers obtained (in which MONIS 2, the more valuable isomer, is only formed to the extent of about 22%) as in the potential danger involved in the use of the ternary nitrating mixture $HNO_3$/acetic acid/acetic anhydride. DUBAR and CALZIA, Comptes Rendus de l'Académie des Sciences de Paris, Volume 266, 1,114–1,116, Series C, Apr. 8, 1968, in fact showed that such mixtures, and especially those containing, in particular, nitric acid and acetic anhydride, contain acetyl nitrate, which is considered to be a more sensitive explosive than nitroglycerine. Medard, in his work "Les Explosifs Occasionnels", ("Potential Explosives"), Volume 2, p. 486–487 (1978), has more recently again warned users of such mixtures against the danger of explosion, the consequences of which are the more serious, the greater the proportion of the suspect nitrating mixture in the reaction mixture.

A second process has been proposed, which is described in U.S. Pat. No. 4,065,488. This process consists in forming a mixture of isosorbitol monoacetates and diacetates in a first stage, then in nitrating this mixture with the aid of a mixture of concentrated nitric acid and acetic anhydride, and finally in hydrolysing the mixture obtained and in isolating MONIS 2. This process has the advantage that it leads to a mixture of isomers in which MONIS 2 is preponderant, relative to MONIS 5, but this advantage is offset by serious disadvantages, namely a relatively low yield, a very long reaction time (2 to 5 days), a large number of steps and, in particular, the use of a potentially explosive nitrating mixture, especially if the proportions are incorrect.

Despite its substantial disadvantages, the latter process has seemed to be the safer hitherto, because of the fact, which should be stressed, that it only involves the formation of small amounts of DINIS, which is a known explosive.

Thus, there is no process available at the present time which is safe and as inexpensive as possible, and which leads to good yields of MONIS 2.

Applicants' has now found a process which makes it possible to solve the problem presented.

The invention consists of a process for the synthesis of isosorbide mononitrates, characterised in that isosorbide dinitrate is denitrated by means of a hydrazine derivative, in a polar solvent medium.

In fact, it has been found that, contrary to all expectations, it is possible under certain conditions to eliminate any danger of explosion in the handling of DINIS, in contrast to the opinions held, to decompose DINIS into MONIS compounds without the decomposition reaching the isosorbitol stage, and to direct the denitration towards the preferential formation of MONIS 2. This is very surprising because the use of other means of partial hydrolysis, such as pyridine or sulphuric acid, leads precisely to that which can normally be expected, namely mixtures of DINIS, MONIS compounds and isosorbitol, and, in the MONIS compounds obtained, to a high proportion of MONIS 5 since this isomer is the one which results from the hydrolysis of the more accessible of the nitrate groups of DINIS.

The conditions demonstrated according to the invention are essentially those which have just been mentioned, namely the use of a hydrazine derivative and a polar solvent medium.

The term "hydrazine derivative" must be understood as meaning, in particular, hydrazine and the compounds which are derived from the latter by substitution of at least one and at most three of the hydrogen atoms which it carries on its nitrogen atoms, by hydrocarbon groups such as aliphatic groups containing from 1 to 10 carbon atoms, aromatic groups containing from 6 to 12 carbon atoms, which are optionally substituted, in particular by halogen atoms, amino groups or nitro groups, aliphatic-aromatic groups such as the benzyl group, and acyl groups such as the acetyl or benzoyl group.

In general, it is preferred, within the scope of the present invention, to use a hydrazine derivative of the type known for being a normally effective reducing agent, and, in this respect, the invention also comprises the use of addition compounds of hydrazines, in particular the hydrates and hydrochlorides.

Thus, the following are readily used: hydrazine, hydrazine hydrate, and also mono-substituted or di-substituted hydrazines such as monomethylhydrazine, N,N'-dimethylhydrazine, N,N-dimethylhydrazine, monophenylhydrazine at their hydrates, and preferably, in general, those hydrazines which give rise to the formation of the smallest possible amount of products capable of reducing the polarity of the reaction medium after reaction with DINIS. In this connection, it is also preferred to avoid the use of those hydrazine derivatives which, after reaction, give rise to the formation of solid or liquid compounds capable of forming an additional phase in the reaction medium, which, as stated, comprises a polar solvent medium.

It has been surprisingly found that the mono or di(alkyl or phenyl)-substituted hydrazines and their addition compounds and preferably the di(alkyl or phenyl)-substituted hydrazines and their addition compounds such as N.N-dimethyl hydrazine enabled to get better ratios.

The term "polar solvent medium" must be understood as meaning a medium having at least one phase containing a solvent or a mixture of solvents which has both a good solvent power in respect of DINIS and the hydrazine derivative, and a dielectric constant of more than 3 at 20° C. According to the invention, it is thus possible to use a heterogeneous mixture of solvents in which only one of the phases satisfies the polarity condition indicated above. However, a medium consisting of a single phase is suitable. Of particular value is a mixture of polar solvents of different proticity, in which, for example, one solvent is protic and the other is not.

Examples of mixtures of this type consist of mixtures of aromatic compounds and aliphatic alcohols, such as toluene-ethanol, toluene-propanol, toluene-methanol, benzene-ethanol, benzene-methanol or benzene-propanol mixtures, or mixtures of ethers and aliphatic alcohols, such as THF-ethanol, dioxane-methanol, dioxane-ethanol or THF-methanol mixtures, these last two mixtures being particularly preferred.

The DINIS used as a starting material, within the scope of the present invention, is an explosive compound having well-known detonating characteristics. Applicants have been able to observe that the handling of DINIS does not present any difficulty from the point of view of safety, provided that this product is damp or impregnated with solvent, or in solution, so that it is not necessarily advantageous to isolate the DINIS which has just been synthesised, before treating it with a hydrazine derivative according to the invention.

In principle, it is possible to use the stoichiometric proportion of hydrazine derivative, relative to the DINIS. In practice, 1 to 2 mols or more of hydrazine derivative is used per mol of DINIS, preferably from 1.1 to 1.5 mols. Naturally, this molar proportion must be determined according to the number of effective hydrazine groups carried by the hydrazine derivative, if the latter is a polyhydrazine compound.

The temperature prevailing in the reaction medium is not a very critical factor, but, to obtain an industrially satisfactory reaction time, it is preferable to carry out the reaction according to the invention at a temperature above 40° C., preferably above 60° C., but below and preferably at the reflux temperature of the solvent medium used, which is generally of the order of 65° C. and must not under any circumstances exceed 150° C.

Naturally, the scope of the present invention is not exceeded by the use of catalysts for the hydrolysis by the hydrazine derivatives. Examples of such catalysts which may be mentioned are palladium, platinum, and also strong bases such as sodium ethoxide. However, the reaction is generally sufficiently rapid in the absence of catalysts, so that catalysts can easily be dispensed with.

The order of introduction of the reactants is not a critical factor in the process according to the invention. However, it is preferable initially to form a solution of DINIS in the polar solvent medium, and only then to introduce the hydrazine derivative, pure or in solution. The introduction is an operation which can be carried out within a few minutes, for example, in 15 minutes, and this is advantageous from the point of view both of the time saved and of the quality of the products obtained. When the introduction is complete, the reaction medium requires no further attention. The reaction medium can be stirred, if appropriate, and this can be achieved either mechanically or by carrying out the reaction at the reflux temperature of the solvent, the latter appearing to be the more advantageous solution, as stated above. The reaction can be considered to be complete after 1 to 10 hours, depending on the conditions, and more generally after 2 to 7 hours, which makes it possible to apply the process continuously, if desired. The solvent is then driven off, for example in vacuo, and the reaction medium is filtered, if necessary, in order to remove the DINIS which may not have reacted and has therefore precipitated. The residue contains the MONIS compounds to the exclusion of appreciable amounts of any other by-products. The residue is taken up in water, and the aqueous phase thus obtained is extracted with an organic solvent for the MONIS compounds, such as a chlorinated aliphatic hydrocarbon. After the solvent has been evaporated off, a yellow-coloured oil consisting of MONIS 2 and MONIS 5 is obtained, which is separated by any conventional separation process, in particular by fractional crystallisation or by chromatography. The latter method can advantageously be applied in silica-filled columns of large diameter, the elution solvent advantageously being the pair $CCl_4$/acetone in the ratio 4:1.

Thus, the amount of MONIS 2 obtained is about twice that of MONIS 5, the overall yield of the reaction varying, according to the conditions selected, between 15 and 60% by weight of MONIS 2, relative to the starting DINIS. The MONIS 2 obtained under the conditions of the invention has an advantageous purity straightaway, since it has a melting point of between 52.5° and 53° C. after the separation and a melting point above or equal to 54° C. after a first recrystallisation carried out on the product isolated.

As the process according to the invention leads to a mixture which only contains the two desired isomers, the MONIS 5 is also easily collected directly in the form of a white solid melting at 89° C., which is consistent with the literature indications for the pure product.

The invention will be understood more clearly with the aid of the following example, which illustrates the present invention without limiting it:

EXAMPLE 1

150 ml of THF, 150 ml of methanol and 59.0 g (0.25 mol) of DINIS are mixed in a 500 ml Keller reactor fitted with a stirrer, a reflux condenser and and dropping funnel.

The stirring is started and the mixture is heated to the reflux temperature.

When the reflux temperature has been reached, 17.5 g (0.35 molar) (that is to say a 40% molar excess relative to the DINIS) of hydrazine hydrate are run into the medium in the course of 15 minutes. When the introduction is complete, reflux is maintained for 3 hours. The heating is stopped, the solvents are evaporated off in vacuo and the precipitate formed, which consists of re-usable DINIS, is filtered off. The liquid phase is taken up in 150 ml of water and then extracted with four times 50 ml of chloroform. The organic phases are combined and the chloroform is evaporated off in vacuo: a yellow oil is obtained which solidifies slowly and which appears to consist solely of MONIS 2 and MONIS 5.

The two isomers were separated on a column of internal diameter 45 mm and height 50 cm, filled with Merck silica gel of particle size 0.063 to 0.2 mm (ASTM 70–230

Mesh), the elution solvent being an 80/20 mixture of carbon tetrachloride and acetone.

This yielded, on the one hand, 13.4 g of MONIS 2, that is to say an overall yield of 28%, and, on the other hand, 6.5 g of MONIS 5.

The products had the following spectral and physical characteristics:

| Infra-Red Spectrum | (a) OH | (b) ONO$_2$ | (b) COC |
|---|---|---|---|
| MONIS 2 | 3,553 cm$^{-1}$ | 1,643, 1,272, 845 cm$^{-1}$ | 1,084 cm$^{-1}$ |
| MONIS 5 | 3,620 cm$^{-1}$ | 1,645, 1,280, 845 cm$^{-1}$ | 1,092 cm$^{-1}$ |

(a): 0.1% strength solutions in CCl$_4$, 1 cm Infrasil cells.
(b): 1% strength solutions in benzene, 100 μm NaCl cells.

| Physical Properties | Melting Point (°C.) | Optical Rotation (c) | DTA (d) |
|---|---|---|---|
| MONIS 2 | 54.0 | 71.0° | 57°–168° C. |
| MONIS 5 | 88.9 | 173.5° | 94°–173° C. |

(c): Value of n$_D^{23°}$ for a 2% strength solution in ethyl acetate.
(d): Differential Thermal Analysis: The first value indicated corresponds to an endothermic peak (melting) and the second corresponds to an exothermic peak (decomposition).

EXAMPLE 2

Following the procedure of Example 1, 300 ml of dioxane, 300 ml of methanol and 118.0 g (0.5 mol) of DINIS are mixed.

When the reflux temperature has been reached, 35.0 g (0.7 mol) of hydrazine hydrate are run in, in the course of 30 minutes. Reflux is maintained for 6 hours. After the solvents have been evaporated off in vacuo, the DINIS filtered off and the product purified, a mixture of MONIS 2 and MONIS 5 is obtained with the yield of 51%. The proportion of the two isomers is identical to that in Example 1.

EXAMPLE 3

Following the procedure of Example 1, 300 ml of dioxane, 300 ml of ethanol and 118.0 g (0.5 mol) of DINIS are mixed. When the reflux temperature has been reached, 35.0 g (0.7 mol) of hydrazine hydrate are run in, in the course of 1 hour. Reflux is maintained for 5 hours. After the solvents have been evaporated off in vacuo, the DINIS filtered off and the product purified, a mixture of MONIS 2 and MONIS 5 is obtained, in the same proportions as above, with a yield of 50%.

EXAMPLE 4

Two experiments were carried out with a toluene/ethanol mixture in different proportions:
(a) toluene 70/ethanol 30 (in ml)
(b) toluene 30/ethanol 70

The procedure is identical to the above procedures, that is to say that the same proportions of DINIS and hydrazine hydrate are used in 600 ml of solvent.

The introduction is carried out in the course of 1 hour and reflux is maintained for 5 hours. After the evaporation, filtering and purification operations, a mixture of MONIS 2 and MONIS 5 is obtained, in the same proportions as above, respectively with the following yields:
19% for solvent (a)
38% for solvent (b)

EXAMPLE 5

An experiment identical to Example 3 was carried out, the hydrazine hydrate being replaced by N,N-dimethylhydrazine hydrate (or UDMH). 300 ml of dioxane, 300 ml of ethanol and 118.0 g (0.5 mol) of DINIS are mixed. When the reflux temperature has been reached, 35.0 g (0.7 mol) of N,N-dimethylhydrazine hydrate, in solution in a mixture of 10 ml of ethanol and 10 ml of dioxane, are run in. After evaporation, filtering and purification, a mixture of MONIS 2 and MONIS 5 is obtained, in the same proportions as above, with a yield of 80%.

EXAMPLE 6

Following the procedure of Example 1, 600 ml of ethanol and 118.0 g (0.5 mol) of DINIS are mixed. When the reflux temperature has been reached, 35.0 g (0.7 mol) of hydrazine hydrate are run in, in the course of 1 hour. Reflux is maintained for 5 hours. After the solvents have been evaporated off in vacuo, the DINIS filtered off and the product purified, a mixture of MONIS 2 and MONIS 5 is obtained, in the same proportions as above, with a yield of 38%.

We claim:

1. Process for the synthesis of isosorbide mononitrates, characterised in that isosorbide dinitrate is denitrated by means of a hydrazine derivative, in a polar solvent medium.

2. Process according to claim 1, wherein the hydrazine derivative is a member selected from the group consisting of hydrazine and compounds derived from the latter by substitution of at least one and up to three of the hydrogen atoms which it carries on its nitrogen atoms, by (a) an hydrocarbon group which is a substituted or unsubstituted aliphatic group containing from 1 to 10 carbon atoms, a substituted or unsubstituted aromatic group containing from 6 to 12 carbon atoms, the substituent being halogen, amino or nitro, (b) benzyl, (c) acyl and a hydrate or a hydrochloride thereof.

3. Process according to claim 1, wherein the polar solvent medium is a medium having at least one phase containing a solvent or a mixture of solvents which has both a good solvent power in respect of the isosorbide dinitrate and the hydrazine derivative, and a dielectric constant of more than 3° to 20° C.

4. Process according to claim 3, wherein a mixture of solvents of different proticities is used.

5. Process according to claim 4, wherein the mixture is a member selected from the group consisting of THF-ethanol, dioxane-methanol, dioxane-ethanol and THF-methanol mixtures.

6. Process according to claim 2, wherein from 1 to 2 mols of hydrazine derivative are used per mol of isosorbide dinitrate.

7. Process according to claim 1, wherein the reaction is carried out at a temperature which is above 40° C. up to the reflux temperature of the solvent medium used.

8. Process according to claim 1, characterised in that a catalyst is used for the hydrolysis by the hydrazine derivatives.

9. Process according to claim 1, characterised in that a solution of the isosorbide dinitrate in the polar solvent medium is initially made up and the hydrazine derivative is then introduced into the said mixture, heated to the reflux temperature of the solvent medium.

10. Process according to claim 9, characterised in that the hydrazine derivative is introduced in the course of about 15 minutes.

11. Process according to claim 1 characterized in that the hydrazine derivative is a member selected from the group consisting of the mono- or di-alkyl, phenyl-substituted hydrazine and their additional compounds.

12. The process according to claim 11 wherein the hydrazine derivative is a dialkyl or phenyl-substituted hydrazine and addition products thereof.

* * * * *